(12) United States Patent
Esch et al.

(10) Patent No.: US 7,247,168 B2
(45) Date of Patent: Jul. 24, 2007

(54) ACCOMMODATING INTRAOCULAR LENS SYSTEM AND METHOD

(75) Inventors: Victor Esch, Albuquerque, NM (US); Barry Cheskin, Mountain View, CA (US); John Scholl, Danville, CA (US); Henry Wu, Diamond Bar, CA (US); David Smith, Highland, CA (US); Bill Evans, San Francisco, CA (US); Patrick Myall, San Francisco, CA (US); Terry Smiley, San Francisco, CA (US)

(73) Assignee: PowerVision, Inc., Belmont, CA (US)

( * ) Notice: Subject to any disclaimer, the term of this patent is extended or adjusted under 35 U.S.C. 154(b) by 66 days.

(21) Appl. No.: 11/173,961

(22) Filed: Jul. 1, 2005

(65) Prior Publication Data
US 2006/0041307 A1    Feb. 23, 2006

Related U.S. Application Data

(63) Continuation-in-part of application No. 10/971,598, filed on Oct. 22, 2004, which is a continuation-in-part of application No. 10/734,514, filed on Dec. 12, 2003, now Pat. No. 7,122,053.

(60) Provisional application No. 60/433,046, filed on Dec. 12, 2002.

(51) Int. Cl.
*A61F 2/16* (2006.01)
(52) U.S. Cl. ...................... 623/6.37; 623/6.13
(58) Field of Classification Search .............. 623/6.11, 623/6.13, 6.34, 6.37, 6.39, 6.4, 6.43, 6.62
See application file for complete search history.

(56) References Cited

U.S. PATENT DOCUMENTS

| | | | |
|---|---|---|---|
| 4,253,199 A | 3/1981 | Banko | |
| 4,373,218 A | 2/1983 | Schachar | |
| 4,512,040 A | 4/1985 | McClure | |
| 4,585,457 A | 4/1986 | Kalb | |
| 4,685,921 A | 8/1987 | Peyman | |
| 4,685,922 A | 8/1987 | Peyman | |
| 4,693,717 A | 9/1987 | Michelson | |
| 4,731,078 A | 3/1988 | Stoy et al. | |
| 4,731,080 A * | 3/1988 | Galin | ................... 623/6.57 |
| 4,816,031 A | 3/1989 | Pfoff | |
| 4,888,012 A | 12/1989 | Horn et al. | |
| 4,892,543 A | 1/1990 | Turely | |
| 4,902,293 A | 2/1990 | Feaster | |
| 4,932,966 A | 6/1990 | Christie et al. | |
| 4,950,289 A | 8/1990 | Krasner | |

(Continued)

FOREIGN PATENT DOCUMENTS

WO    WO 2004/010895    2/2004

*Primary Examiner*—William H Matthews
(74) *Attorney, Agent, or Firm*—Shay Law Group LLP

(57) ABSTRACT

An accommodating intraocular lens is provided having optical parameters that are altered in-situ, wherein an optic portion of the lens includes an actuator that deflects a lens element to alter the optical power of the lens, responsive to forces applied to a haptic portion to the lens by contraction of the ciliary muscles. Forces applied to the haptic portion may result in fluid displacements from or to the haptic portion from the actuator. Displacement of fluid to the actuator may either increase or reduce the degree of deflection imposed on the lens element by the actuator.

40 Claims, 5 Drawing Sheets

U.S. PATENT DOCUMENTS

| | | | |
|---|---|---|---|
| 4,994,082 A | 2/1991 | Richards et al. | |
| 5,213,579 A | 5/1993 | Yamada et al. | |
| 5,275,623 A | 1/1994 | Sarfarazi | |
| 5,443,506 A | 8/1995 | Garabet | |
| 5,489,302 A | 2/1996 | Skottun | |
| 5,578,081 A | 11/1996 | McDonald | |
| 5,843,188 A | 12/1998 | McDonald | |
| 5,984,962 A | 11/1999 | Anello et al. | |
| 6,013,101 A | 1/2000 | Israel | |
| 6,117,171 A | 9/2000 | Skottun | |
| 6,217,612 B1 | 4/2001 | Woods | |
| 6,299,641 B1 | 10/2001 | Woods | |
| 6,616,691 B1 | 9/2003 | Tran | |
| 6,638,306 B2 | 10/2003 | Cumming | |
| 6,645,245 B1 | 11/2003 | Preussner | |
| 6,660,035 B1 | 12/2003 | Lang et al. | |
| 6,692,525 B2 | 2/2004 | Brady et al. | |
| 6,695,881 B2 | 2/2004 | Peng et al. | |
| 6,712,848 B1 | 3/2004 | Wolf et al. | |
| 6,730,123 B1 | 5/2004 | Klopotek | |
| 7,068,439 B2 * | 6/2006 | Esch et al. | 359/666 |
| 2001/0016771 A1 | 8/2001 | Cumming | |
| 2003/0050695 A1 | 3/2003 | Lin et al. | |
| 2003/0149480 A1 | 8/2003 | Shadduck | |
| 2004/0006387 A1 | 1/2004 | Kelman | |
| 2004/0015236 A1 | 1/2004 | Sarfarazi | |
| 2004/0039446 A1 | 2/2004 | McNicholas | |
| 2004/0054408 A1 | 3/2004 | Glick et al. | |
| 2004/0082994 A1 | 4/2004 | Woods et al. | |
| 2004/0085511 A1 | 5/2004 | Uno et al. | |
| 2004/0111151 A1 | 6/2004 | Paul et al. | |
| 2004/0111152 A1 | 6/2004 | Kelman | |
| 2004/0127984 A1 | 7/2004 | Paul et al. | |
| 2004/0162612 A1 | 8/2004 | Portney et al. | |
| 2004/0181279 A1 | 9/2004 | Nun | |
| 2005/0119740 A1 * | 6/2005 | Esch et al. | 623/6.37 |

* cited by examiner

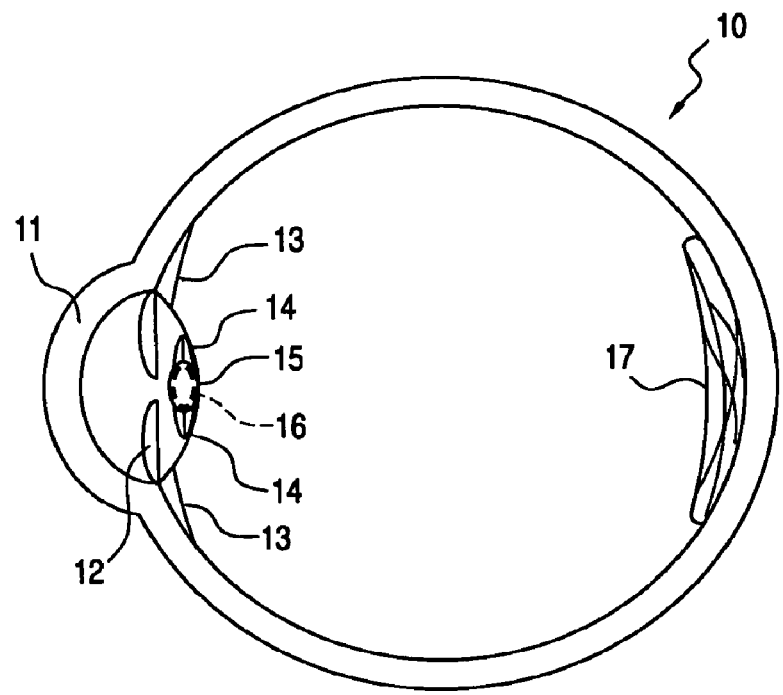
FIG.1
FIG.2A
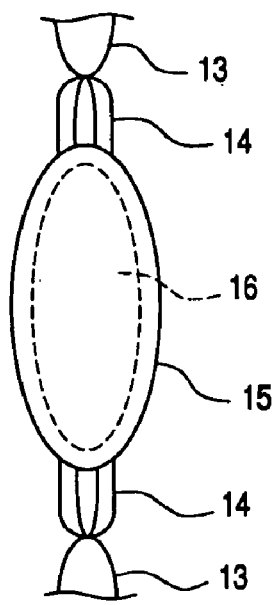
FIG.2B
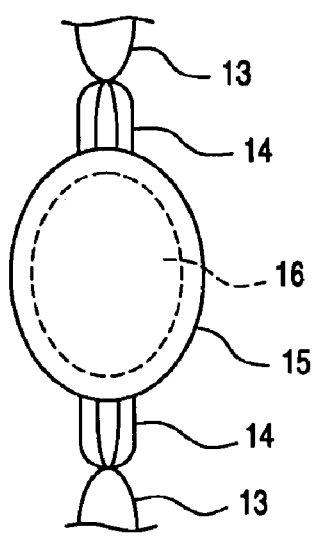

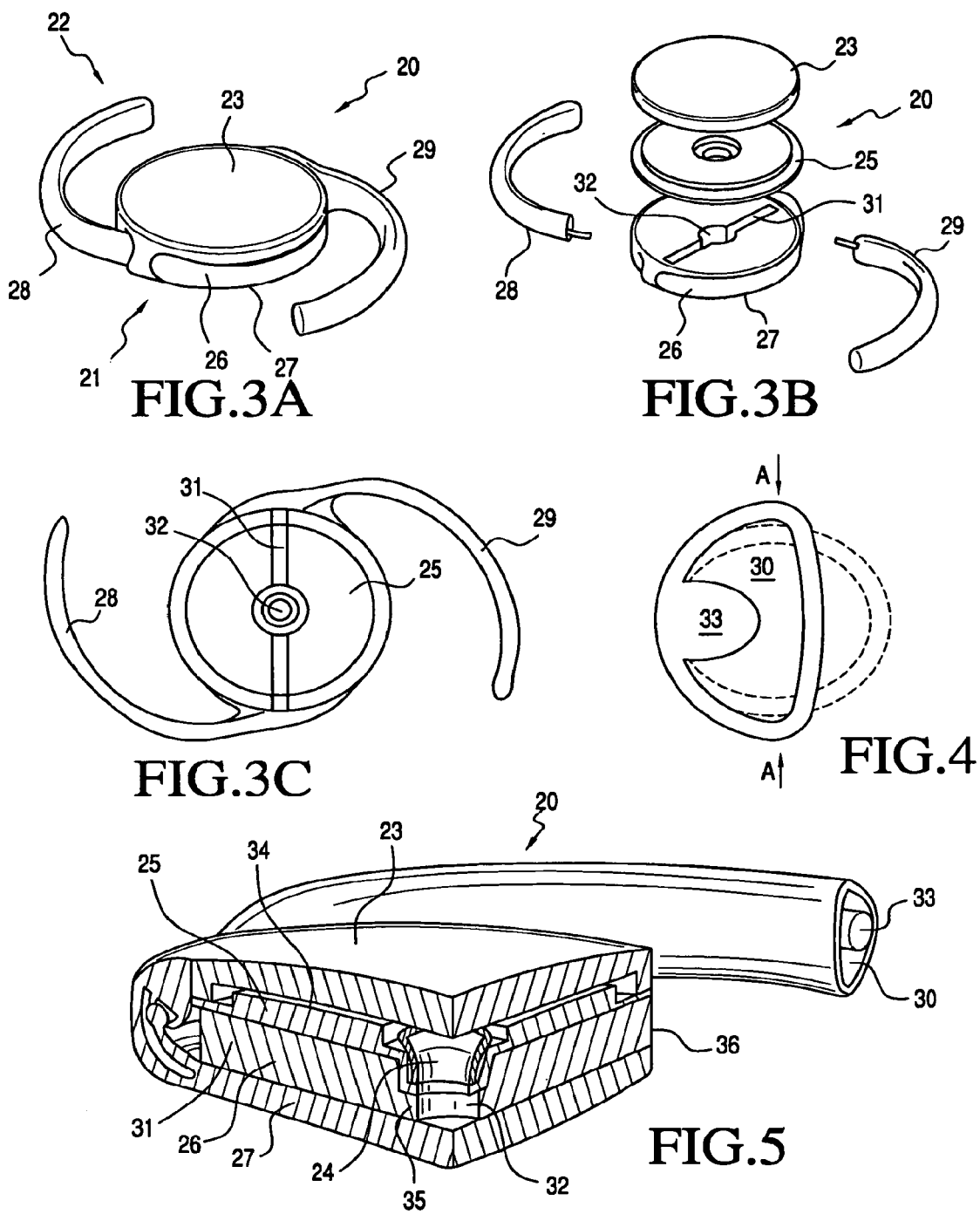

ACCOMMODATING INTRAOCULAR LENS SYSTEM AND METHOD

REFERENCE TO RELATED APPLICATIONS

This application is a continuation-in-part of U.S. patent application Ser. No. 10/971,598, filed Oct. 22, 2004, which is a continuation-in-part of U.S. patent application Ser. No. 10/734,514, filed Dec. 12, 2003, now issued as U.S. Pat. No. 7,122,053 and claims the benefit of priority from U.S. provisional patent application Ser. No. 60/433,046, filed Dec. 12, 2002.

FIELD OF THE INVENTION

The present invention relates to intraocular lenses ("IOLs") having optical parameters that are changeable in-situ. More particularly, the invention has application in IOLs for in-capsule implantation for cataract patients, wherein movement of the ciliary muscles induces transfer of fluid media within the interior of the IOL, thereby altering an optical power of the lens to provide accommodation.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule supported by the ciliary muscles, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein), move between a relaxed state (corresponding to the moderately convex shape) and a contracted state (corresponding to the highly convex shape). Because the lens itself is composed of viscous, gelatinous transparent fibers, arranged in an "onion-like" layered structure, forces applied to the capsule by the ciliary muscles cause the lens to change shape.

Isolated from the eye, the relaxed capsule and lens take on a spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter-muscular mode. Accordingly, when the ciliary muscles are relaxed, the capsule and lens are pulled about the circumference to a larger diameter, thereby flattening the lens, whereas when the ciliary muscles are contracted the lens and capsule relax somewhat and assume a smaller diameter that approaches a more spherical shape.

As noted above, the youthful eye has approximately 14 diopters of accommodation. As a person ages, the lens hardens and becomes less elastic, so that by about age 45–50, accommodation is reduced to about 2 diopters. At a later age the lens may be considered to be non-accommodating, a condition known as "presbyopia". Because the imaging distance is fixed, presbyopia typically entails the need for bi-focals to facilitate near and far vision.

Apart from age-related loss of accommodation ability, such loss is innate to the placement of IOLs for the treatment of cataracts. IOLs are generally single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability.

Although previously known workers in the field of accommodating IOLs have made some progress, the relative complexity of the methods and apparatus developed to date have prevented widespread commercialization of such devices. Previously known these devices have proved too complex to be practical to construct or have achieved only limited success, due to the inability to provide accommodation of more than 1–2 diopters.

U.S. Pat. No. 5,443,506 to Garabet describes an accommodating fluid-filled lens wherein electrical potentials generated by contraction of the ciliary muscles cause changes in the index of refraction of fluid carried within a central optic portion. U.S. Pat. No. 4,816,031 to Pfoff discloses an IOL with a hard PMMA lens separated by a single chamber from a flexible thin lens layer that uses microfluid pumps to vary a volume of fluid between the PMMA lens portion and the thin layer portion and provide accommodation. U.S. Pat. No. 4,932,966 to Christie et al. discloses an intraocular lens comprising a thin flexible layer sealed along its periphery to a support layer, wherein forces applied to fluid reservoirs in the haptics vary a volume of fluid between the layers to provide accommodation.

Although fluid-actuated mechanisms such as described in the aforementioned patents have been investigated, currently available accommodating lenses, such as developed by Eyeonics, Inc. (formerly C&C Vision, Inc.) of Aliso Viejo, Calif., employ a substantially rigid frame configured to vault posteriorly responsive to ciliary muscle contraction, thereby moving the optic towards or away from the retina to adjust the focus of the device.

In view of the foregoing, it would be desirable to provide apparatus and methods that restore appropriate optical focusing power action to the human eye.

It further would be desirable to provide methods and apparatus wherein a dynamic lens surface may be effectively manipulated responsive to movements of the ciliary muscles.

It still further would be desirable to provide methods and apparatus that utilize forces arising due to natural accommodating muscular action to induce deflection of an optical surface of the IOL. In particular, it would be desirable to provide an IOL in which muscle movements result in the application of, or removal of, forces to the IOL so as to operate one or more actuators to cause deflection of the dynamic surface.

SUMMARY OF THE INVENTION

In view of the foregoing, it is an object of the present invention to provide apparatus and methods that restore appropriate optical focusing power action to the human eye.

It is a further object of this invention to provide methods and apparatus wherein a dynamic lens surface may be effectively manipulated responsive to movement of the ciliary muscles.

It is another object of the present invention to provide methods and apparatus that utilize forces arising due to natural accommodating muscular action to induce deflection of an optical surface of the IOL.

It is a further object of this invention to provide methods and apparatus for reversibly communicating forces arising due to muscle movement to a dynamic surface via one or more actuators, thereby altering the optical parameters of one of more surfaces of the IOL.

These and other objects of the present invention are accomplished by providing an intraocular lens responsive to forces communicated from the ciliary muscles through the capsular bag to operate one or more actuators disposed within the IOL. The actuator is coupled to a dynamic surface of the IOL to deflect the dynamic surface, e.g., from a moderately convex to a highly convex shape, responsive to operation of the one or more actuators. In accordance with the principles of the present invention, the IOL includes at least one fluid-mediated actuator coupled to a fluid column disposed in at least one haptic of the IOL. Forces applied to the haptic by the capsular bag, responsive to movement of the ciliary muscles, cause the transfer of fluid between the fluid column and the actuator, which in turn deflects a dynamic surface of the lens.

In a preferred embodiment, the intraocular lens comprises an optic portion and a haptic (or non-optic) portion. The optic portion comprises a light transmissive substrate defining one or more fluid channels, at least one actuator coupled in fluid communication with the fluid channels, and anterior and posterior lens elements. One of the anterior and posterior lens elements includes a dynamic surface that is operatively coupled to the actuator to cause deflection of the dynamic surface. The other of the anterior or posterior lens elements may be coupled to the substrate or integrally formed therewith.

The haptic portion is disposed at the periphery of the optic portion and comprises one or more haptics that extend outward from the optic portion, each haptic including a fluid channel coupled in fluid communication with a fluid channel in the optic portion. In accordance with one aspect of the present invention, the haptics have a cross-sectional configuration selected so that the internal volume of the haptic is small in an unstressed state. The unstressed state is selected to correspond to the accommodated state of the eye, when the ciliary muscles are contracted and lateral forces applied by the capsular bag to the haptics are minimal. When the ciliary muscles relax, the zonules pull the capsular bag taut and apply forces to the lateral faces of the haptic. These forces cause the cross-sectional area of the haptic to increase and increase the internal volume of the haptic. This action in turn causes fluid to be withdrawn from the actuator disposed in the optic portion, so that the dynamic surface of the IOL transitions from an accommodated state to an unaccommodated state.

For such an embodiment, the actuator used in the optic portion of the IOL may comprise a bellows centrally located within the optic portion that, when filled with fluid, biases the dynamic surface of the IOL to the accommodated state. When the ciliary muscles are contracted, the zonules and capsular bag remain loose, and the haptics are unstressed. Relaxation of the ciliary muscle causes the zonules to transition the capsule to an ellipsoidal shape, which applies compressive forces to the haptic, thereby withdrawing fluid from the actuator and causing the lens to transition to the unaccommodated state. Alternatively, the actuator may comprise bellows-shaped structures disposed at the periphery of the optic portion, so as to minimize refractive effects and optical aberrations in the optic portion.

In an alternative embodiment, the haptic portion comprises one or more haptics having maximal internal volume in the unstressed state, wherein the internal volume of the haptic decreases when compressive forces are applied to the lateral faces of the haptic. In this case, compression of the haptic causes fluid to be transferred into the actuator when the ciliary muscles relax. For such an embodiment, the actuator disposed in the optic portion is reverse-acting, in the sense that operation of the actuator causes the dynamic surface of the IOL to deflect to lower optical power.

Reverse-acting actuators may comprise, for example, a fluid-filled primary bellows that deflects the dynamic surface to an accommodated state when the haptics are unstressed. A secondary bellows may be coupled to the primary bellows and in fluid communication with the haptic portion. Accordingly, when the ciliary muscles relax, the capsule bag tautens and the lateral faces of the haptics are compressed. This causes fluid to be transferred from the haptics to the secondary bellows. As the secondary bellows expands, it lowers the pressure in the primary bellows, and reduces the deflection of the dynamic surface. Alternatively, a reverse-acting actuator may comprise a hollow cylindrical structure coupled to the dynamic surface, where the cylindrical structure is configured to shorten when fluid is introduced into its interior.

In addition, the optic portion may include any of a number of additional features. Such features may include expandable reservoirs to accommodate fluid volumes expelled during disaccommodation of the lens or a constant volume configuration that simply redistributes fluid volumes to change the optical power of the lens. Alternatively, or in addition, the optic portion may include a fulcrum arrangement configured to multiply the volumetric changes induced by fluid transfers between the haptic portion and optic portion. The IOL also may include a barrier coating on either its internal fluid channels and/or the exterior of the lens to reduce diffusion of fluid into the polymer matrix of the lens.

Methods of making and using the lens of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIG. 1 is a sectional side view of a human eye;

FIGS. 2A and 2B are, respectively, sectional side views of the lens and supporting structures of FIG. 1 illustrating relaxed and contracted states of the ciliary muscles;

FIGS. 3A–3B are, respectively, a perspective, exploded perspective and plan view of an exemplary intraocular lens of the present invention;

FIG. 4 is a cross-sectional view of a haptic of the intraocular lens of FIG. 3;

FIG. 5 is a cross-sectional view of the assembled intraocular lens of FIG. 3;

DETAILED DESCRIPTION OF THE INVENTION

Figure 6A:
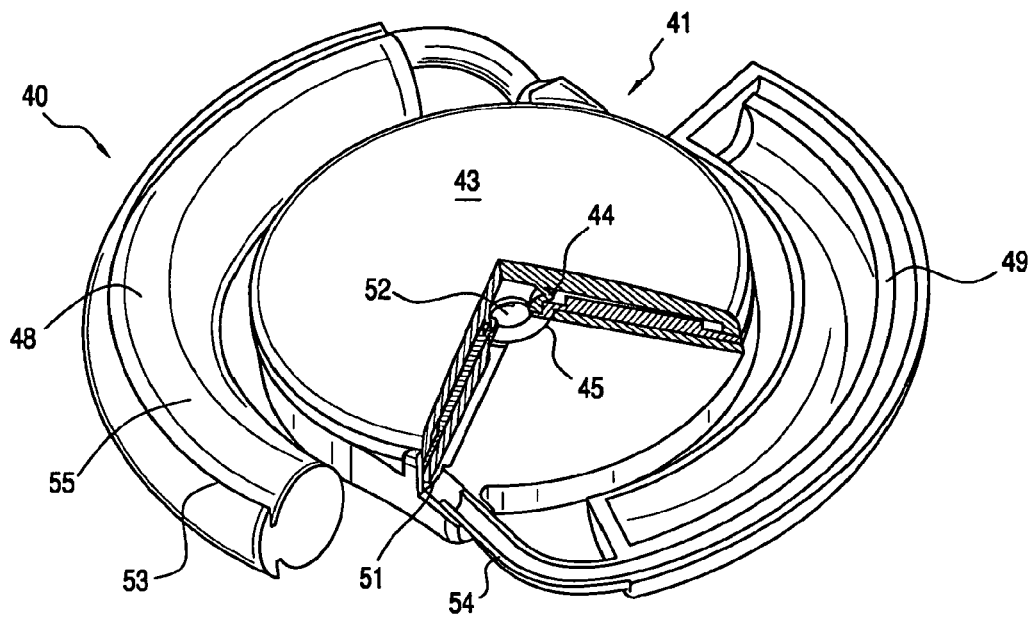
FIGS. 6A–6B are, respectively, a perspective view of an alternative embodiment of the lens of FIG. 3, partly in section, and a perspective sectional view of the haptic of the intraocular lens of FIG. 6A.

In accordance with the principles of the present invention, an intraocular lens is provided having a haptic portion and a light-transmissive optic portion. The optic portion contains one or more fluid-mediated actuators arranged to apply a deflecting force on a dynamic surface of the lens to provide accommodation. As used herein, the lens is fully "accommodated" when it assumes its most highly convex shape, and fully "unaccommodated" when it assumes its most flattened, least convex state. The lens of the present invention is capable of dynamically assuming any desired degree of accommodation between the fully accommodated state and fully unaccommodated state responsive movement of the ciliary muscles.

Forces applied to a haptic portion of the intraocular lens by movement of the ciliary muscles are communicated to at least one actuator that control deflection of a dynamic surface, which may comprise an anterior or posterior element of the lens. The lens actuator and surrounding fluids all are index-matched to prevent the occurrence of optical aberrations and reflections throughout the range of motion of the actuator and dynamic surface.

Referring to FIGS. 1 and 2, the structure and operation of a human eye are first described as context for the present invention. Eye 10 includes cornea 11, iris 12, ciliary muscles 13, ligament fibers or zonules 14, capsule 15, lens 16 and retina 17. Natural lens 16 is composed of viscous, gelatinous transparent fibers, arranged in an "onion-like" layered structure, and is disposed in transparent elastic capsule 15. Capsule 15 is joined by zonules 14 around its circumference to ciliary muscles 13, which are in turn attached to the inner surface of eye 10. Vitreous 18 is a thick, transparent substance that fills the center of eye 10.

Isolated from the eye, the relaxed capsule and lens takes on a spherical shape. However, when suspended within the eye by zonules 14, capsule 15 moves between a moderately convex shape (when the ciliary muscles are relaxed) and a highly convex shape (when the ciliary muscles are contracted). As depicted in FIG. 2A, when ciliary muscles 13 relax, capsule 15 and lens 16 are pulled about the circumference, thereby flattening the lens. As depicted in FIG. 2B, when ciliary muscles 13 contract, capsule 15 and lens 16 relax and become thicker. This allows the lens and capsule to assume a more spherical shape, thus increasing the diopter power of the lens.

Accommodating lenses that are currently commercially available, such as the Crystalens device developed by Eyeonics, Inc., Aliso Viejo, Calif., typically involve converting movements of the ciliary muscle into anterior and posterior movement of the optic portion of the IOL relative to the retina. Such devices do not employ the natural accommodation mechanisms described above with respect to FIGS. 1–2, but instead rely directly on radially inward compressive forces applied by the ciliary muscle to the haptics of the IOL.

By contrast, according to one aspect of the present invention, an intraocular lens is designed to engage capsule 15 and to transition between the accommodated and unaccommodated states responsive to forces applied to capsule 15 by ciliary muscle 13 and zonules 14, thereby more closely mimicking operation of the natural eye.

Referring now to FIGS. 3–5, an exemplary embodiment of an intraocular lens constructed in accordance with the principles of the present invention is described. IOL 20 comprises optic portion 21 and haptic portion 22. Optic portion 21 is constructed of light transmissive materials, while haptic portion 22 is disposed at the periphery of the optic portion and does not participate in focusing light on the retina of the eye.

Optic portion 21 comprises anterior lens element 23 including actuator 24 (see FIG. 5), intermediate layer 25, substrate 26 and posterior lens element 27, all made of light-transmissive materials, such as silicone or acrylic polymers or other biocompatible materials as are known in the art of intraocular lenses. Illustratively, actuator 24 comprises a bellows structure that is integrally formed with anterior lens element 23, although other arrangements are within the scope of the invention. While optic portion 21 is illustratively described as comprising three layers, it will be apparent that only two layers may be employed, for example, with the intermediate layer, substrate and posterior lens being integrally formed.

Haptic portion 22 illustratively comprises haptics 28 and 29 that extend from substrate 26, although other haptic configurations may be employed. Each of haptics 28 and 29 includes an interior volume 30 that communicates with channel 31 in substrate 26. Actuator 24 is disposed in well 32 formed in intermediate layer 25 and substrate 26, so that a lower end of the actuator seats within well 32. Haptics 28 and 29 may each include a resilient support member 33 (see FIGS. 4 and 5) that urges the haptic radially outward to ensure that the haptic seats against the capsular equator.

Although channel 31 and well 32 are depicted in FIG. 5 having their side walls that disposed parallel to the optical axis of the lens, it is expected that all such surfaces should be arranged obliquely relative to the optical axis of the IOL.

Such an arrangement is expected to reduce the potential to create spurious reflections in light passing along the optical axis of the IOL. It should be understood that such arrangements may be beneficially employed throughout the IOLs described in this specification.

As depicted in FIG. 4, each of haptics 28 and 29 has an undeformed state and may be transitioned to a deformed state (shown in dotted line in FIG. 4) by application of compressive forces to the lateral surfaces of the haptic (shown by arrows A). In accordance with one aspect of the present invention, the interior volume of the haptic increases as the haptic deforms from the undeformed, unstressed state to the deformed state. The undeformed, unstressed state depicted by the solid lines in FIG. 4 corresponds to a fully-contracted state of the ciliary muscles, as described herein below.

Actuator 24 is disposed in well 31 of intermediate layer 25 and substrate 26, and preferably comprises a sturdy elastomeric material. Intermediate layer 25 isolates fluid in channel 31, well 32 and the interior of actuator 24 from the fluid disposed in the space 34 between anterior lens element 23 and intermediate layer 25. Fluids disposed within channels 31 and space 34, preferably comprise silicone or acrylic oils or other suitable biocompatible fluids, and are selected to have refractive indices that match the materials of anterior lens element 23, actuator 24, intermediate layer 25 and substrate 26.

In a preferred embodiment, actuator 24 comprises a bellows structure integrally formed with anterior lens element 23, and is configured to deflect anterior lens element 23 responsive to fluid pressure applied within the bellows by haptics 28 and 29. Alternatively, actuator 24 may be fabricated as a separate component and glued or otherwise bonded to anterior lens element 23 and intermediate layer 25.

Deflection of the anterior lens element resulting from movement of actuator 24 cause the anterior lens element to transition between an accommodated state, in which the lens surface is more convex, to an unaccommodated state, in which the lens surface is less convex. As will of course be understood, optic portion could instead be arranged so that actuator 24 deflects posterior lens element 27. Still further, the actuator may be configured to induce a major deflection of one lens element and a minor deflection of the other lens element; the arrangement depicted in FIG. 3 is intended to be illustrative only.

The inner surface and thickness of anterior element 23 (relative to the optical axis of the lens) are selected so that the outer surface of anterior element 23 retains an optically corrective shape, e.g., spherical, throughout the entire range of motion of actuator 24, e.g., for accommodations 0–10 diopters. It should of course be understood that the inner surface and thickness of anterior element 23 may be selected to provide an aspherical outer surface, as required for a desired degree of optical correction.

As shown in FIGS. 3–5, one preferred embodiment of IOL 20 includes a single actuator 24 located at the center of optic portion 21. Alternative embodiments may include an array of actuators spaced apart in a predetermined configuration on the posterior surface of the anterior lens element, as may be required to impose a desired pattern of localized deflection on the anterior lens element. As will be apparent to one of skill in the art, an annular structure may be substituted for the individual actuator depicted in FIG. 5, and the side walls of the actuator may be of any suitable shape other than a bellows structure. For example, the actuator may comprise a polymer that had been treated, such as bi-axial stress, to pre-orient the polymer to stretch only in a desired direction.

In addition, IOL also may include coating 35 disposed on all interior fluid-contacting surfaces within the IOL, such as fluid channel 31 and well 32 and the surfaces defining space 34. Coating 35 is configured to reduce or prevent diffusion of the index-matched fluid used to drive actuator 24, and within space 34, from diffusing into the polymer matrix of the lens components. The IOL of the present invention also may include coating 36, which may comprise the same or a different material than coating 35, disposed on the exterior surfaces of the lens. Coating 36 is intended to serve as a barrier to prevent the diffusion of fluids from the eye into the IOL, and may be disposed on the entire exterior surface of the optic portion and haptic portion, including the anterior and posterior lens elements and haptics.

Alternatively, both coatings 35 and 36 may be layered onto a single surface to prevent or reduce both ingress of bodily fluids into the IOL or fluid circuit, and loss of index-matched fluid from the interior spaces of the IOL. Coatings 35 and 36 preferably comprise a suitable biocompatible polymer, inorganic (e.g., silicone dioxide) or metallic layer (e.g., nickel-titanium) applied by any of a variety of methods known in the art.

Operation of IOL 20 of FIGS. 3–5 is now described. IOL 20 is implanted within a patient's capsule after extraction of the native lens using any suitable technique. When implanted, haptics 28 and 29 support the IOL so that optic portion 21 is centered along the central axis of eye. When the ciliary muscles are in a contracted state, the zonules and capsule is loose, and the haptics 28 and 29 are in the undeformed state. In this condition, fluid pressure applied by the fluid in the haptics, channel 31 and well 32 maintain actuator 24 fully extended, so that anterior lens element 23 is deflected to its accommodated state.

When the ciliary muscles relax, the zonules pull the capsule taut, thereby applying compressive forces on the lateral surfaces of the haptics. These forces cause the haptics to deform to the deformed state depicted by the dotted lines in FIG. 4, thereby increasing the interior volume of the haptics. Because there is only a predetermined amount of fluid contained within the interior of the haptics, channel 31, well 32 and actuator 24, the increased volume arising in haptics 28 and 29 when deformed draws fluid from within actuator 24. This in turn causes the actuator to shorten, deflecting anterior lens element 23 to a flatter, unaccommodated state. Subsequent contraction and relaxation of the ciliary muscles causes the foregoing process to repeat, thereby providing a degree of lens accommodation that mimics the accommodating action of the natural lens.

Figure 6B:
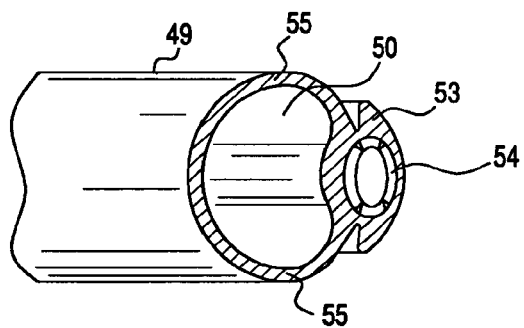

Referring now to FIGS. 6A and 6B, an alternative embodiment of an IOL constructed in accordance with the principles of the present invention is described. Optic portion 41 of IOL 40 is similar in construction to optic portion 21 of the embodiment of FIGS. 3–5. Anterior lens element 43 includes actuator 44, which is seated in a well formed in intermediate layer 45. Haptics 48 and 49 have interior volume 50 and are coupled in fluid communication with channels 51 and well 52 formed in substrate 46.

As depicted in FIG. 6B, each haptic includes support rib 53 that houses a resilient tube 54 and flexible sidewall 55. Rib 53 serves to urge the haptic radially outward to ensure adequate engagement with the capsular equator. In addition, rib 53 may limit the degree of deformation of the lateral sidewalls of the haptic to prevent overdeformation of the haptic that may drive the fluid in the wrong direction. Like the embodiment of FIGS. 3–5, the interior volume of haptics 48 and 49 increases when the capsule compresses the haptics; operation of IOL 40 is similar to that described above for IOL 20.

Figure 7A:
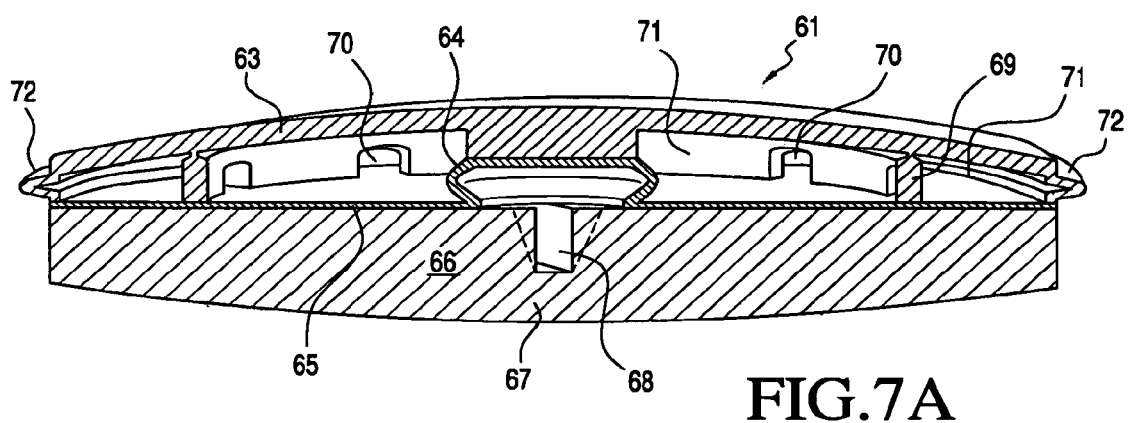
FIGS. 7A–7B are side sectional views of further alternative embodiments of an optic portion of the present invention suitable for use in the intraocular lens of FIGS. 3 and 6.
Figure 7B:
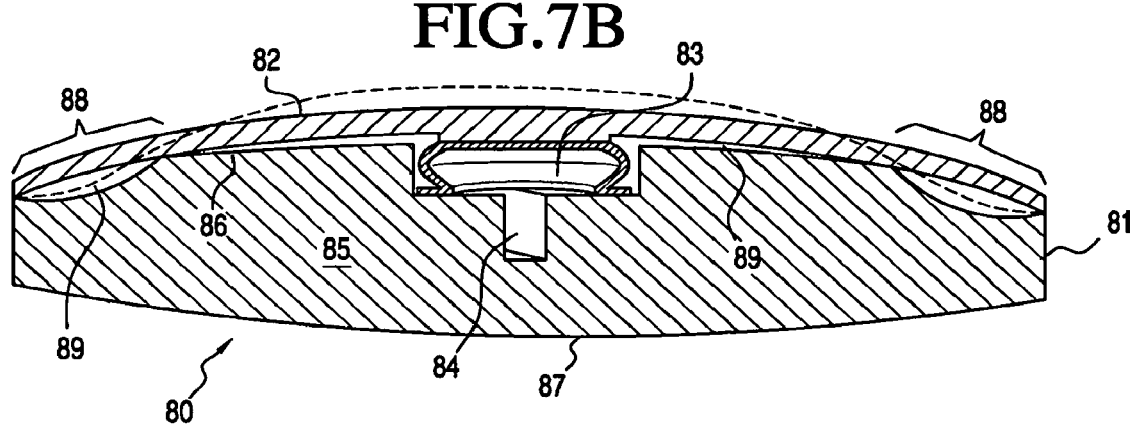

Referring now to FIGS. 7A and 7B, alternative embodiments of optic portions suitable for use with IOLs of the present invention is described. Optic portion 61 includes anterior lens element 63, actuator 64, intermediate layer 65 and substrate 66 with integrally formed posterior lens portion 67. In this embodiment, actuator 64 is integrally formed with intermediate layer 65, or alternatively may be separately fabricated and then bonded to intermediate layer 65. Substrate 66 includes channels 68 that are fluidly coupled to haptics such as described above with respect to FIGS. 4 and 6B.

In the embodiment of FIG. 7A, anterior lens element 63 includes ring-shaped fulcrum 69 that depends from the posterior surface of the anterior lens element. Fulcrum 69 includes a plurality of windows 70 that permit fluid in space 71 to freely move within the space, thus permitting the volume of fluid in space 71 to remain constant, but redistribute between the central portion and peripheral portion of the IOL responsive to the degree of accommodation. As in the preceding embodiments, the fluids in channel 68, actuator 64 and space 71 are index-matched to the surrounding structures to avoid the creation of optical aberrations.

Still referring to FIG. 7A, anterior lens element 63 includes bellows-shaped hinge 72 along its periphery. Fulcrum 69 provides a mechanical advantage by multiplying the deflection achieved for a given amount of fluid displacement. In particular, when the center of anterior lens element 63 deflects inwards during relaxation of the ciliary muscles, fulcrum 69 causes the radially outer regions of the anterior lens element to rotate outwards, thereby achieving a greater degree of flattening of the anterior lens surface then may be achieved for the same amount of fluid displacement in the IOLs of the preceding embodiments. Otherwise, operation of an IOL including optic portion 61 is similar to that described for IOLs 20 and 40 above.

Referring to FIG. 7B, an alternative embodiment of a constant volume accommodating IOL of the present invention is described. IOL 80 comprises optic portion 81 having two-piece construction, suitable for use with the haptics of FIG. 6A. In particular, optic portion 81 comprises anterior lens element 82, actuator 83 coupled to fluid channel 84, and substrate 85. Substrate 85 combines the functions of the intermediate, substrate and posterior lens elements of the embodiment of FIG. 7A. Fluid channel 84 extends to the periphery of the optic portion where it is coupled in fluid communication to the fluid in the interior volumes of the haptics.

In accordance with one aspect of the present invention, substrate 85 includes convex anterior surface 86 having a curvature that provides a predetermined degree of optical correction. Convex surface 86 may be employed either to regularly support anterior lens element 82 in the unaccommodated state, or alternatively only in a fail-safe mode.

In the first case, where convex surface 86 supports anterior lens element 82 in the unaccommodated state, anterior lens element 82 lies flat against convex surface 86 when actuator 83 is in a contracted state, corresponding to the unaccommodated state of IOL 80. Convex surface 86 accordingly results in an unaccommodated degree of optical correction corresponding to the sum of the optical corrections provided by convex surface 86 and posterior surface 87 of substrate 85. For example, posterior lens surface 87 may provide 17 diopters of correction in vivo, while convex surface 86 provides 3 diopters of correction, for a total unaccommodated correction of 20 diopters in vivo.

Actuator 83 is configured to deflect anterior lens element 82 away from convex surface 86 of substrate 85, thereby increasing the optical correction of the anterior lens element. As a central portion of the anterior lens element assumes a more convex shape, the outer periphery of the lens, indicated by zones 88, deflects inward, as indicated by the dotted line in FIG. 7B. Because space 89 between the anterior lens element and the substrate is filled with an fluid that is index-matched to the materials of anterior lens element 82 and substrate 85, deflection of the anterior lens element resulting from movement of actuator 83 does not create an additional diffractive surface. Accordingly, the total power of IOL 80 in the accommodated state is the sum of the powers of the posterior lens surface (17 diopters) plus the optical power of the anterior lens element, which is greater than three. Inward deflection of zones 88 of IOL 80 advantageously permits the volume of fluid in space 89 to remain constant during accommodation, with the fluid becoming redistributed in space 89 responsive to the degree of deflection imposed on anterior lens element 82 by actuator 83.

In addition, convex surface 86 may include radially oriented grooves (not shown) extending from the optical axis to space 89 at the periphery of the optic portion. These grooves permit fluid to flow freely between the posterior surface of anterior lens element 82 and convex surface 86. This arrangement ensures that no vacuum develops between the anterior lens element and convex surface when actuator 83 lifts the anterior lens element away from the convex surface.

Alternatively, anterior lens element 82 may be configured to rest against convex surface 86 only in a fail-safe mode. In this case, anterior lens element 82 is lifted away from convex surface 86 by actuator 83 during normal operation of the IOL. It may be noted that in the foregoing embodiments of the IOL of the present invention, in the undeformed state the haptics maintain the lens in the accommodated or high power state. Accordingly, any failure that allows the actuator to assume the undeformed state without any physiologic influence could result in a residual near-sighted condition. In accordance with another aspect of the present invention, a mechanism is provided to relieve a small amount of quiescent pressure within the lens so that the actuator assumes the unaccommodated, low power state.

In the embodiment of FIG. 7B, this may be accomplished by providing a sacrificial plug on fluid channel 84, near the periphery of the optic portion, that provides separation between the fluid within actuator 83 and channel 84 from the fluid in space 89. The plug preferably comprises a colored material that readily and preferentially absorbs laser light, for example, 1.06 micron wavelength radiation from a Nd:YAG laser. When irradiated, the plug experiences a phase change or otherwise deforms to permit fluid communication between fluid channel 84 and space 89. This in turn permits the fluid pressure within space 89 to equilibrate and dampen movements of actuator 83 corresponding to movements of the ciliary muscles. Advantageously, when the plug is deformed, anterior lens element 82 rests on convex surface 86 of substrate 85 to provide a predetermined optical power, thus ensuring that IOL 80 provides adequate optical correction in the unaccommodated state, but without the near-sightedness that might result from failure of actuator 83 in an extended position.

Alternatively, the sacrificial plug may de disposed on a channel that leads to an evacuated cavity. In this case remodeling of the plug may permit a predetermined quantity of fluid to enter the evacuated space from the fluid channel, again dampening the response of the actuator to fluid transfers resulting from movement of the haptics and ciliary muscles.

Figure 8A:
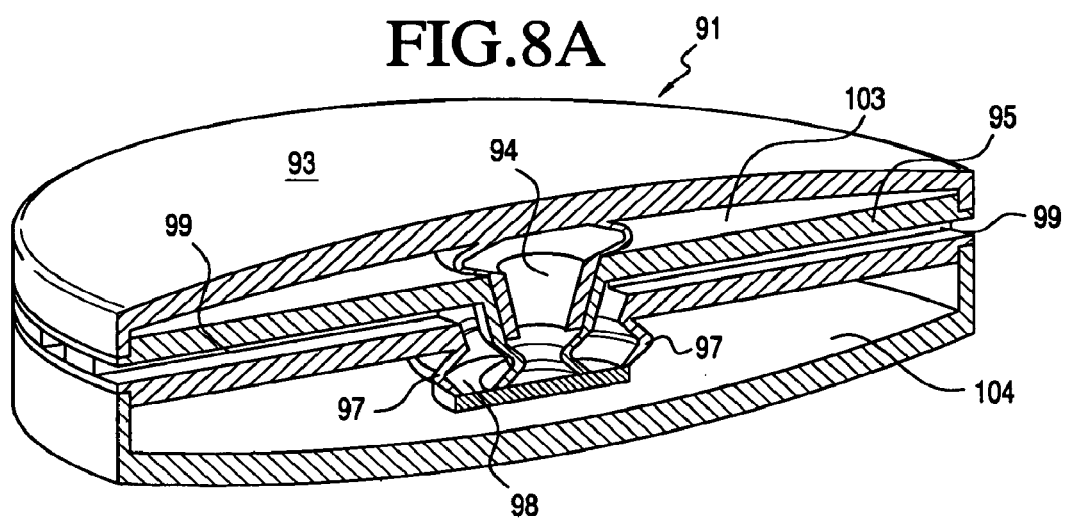
FIGS. 8A–8B are, respectively, perspective side sectional views of an optic portion and intraocular lens of an alternative embodiment of the present invention.
Figure 8B:
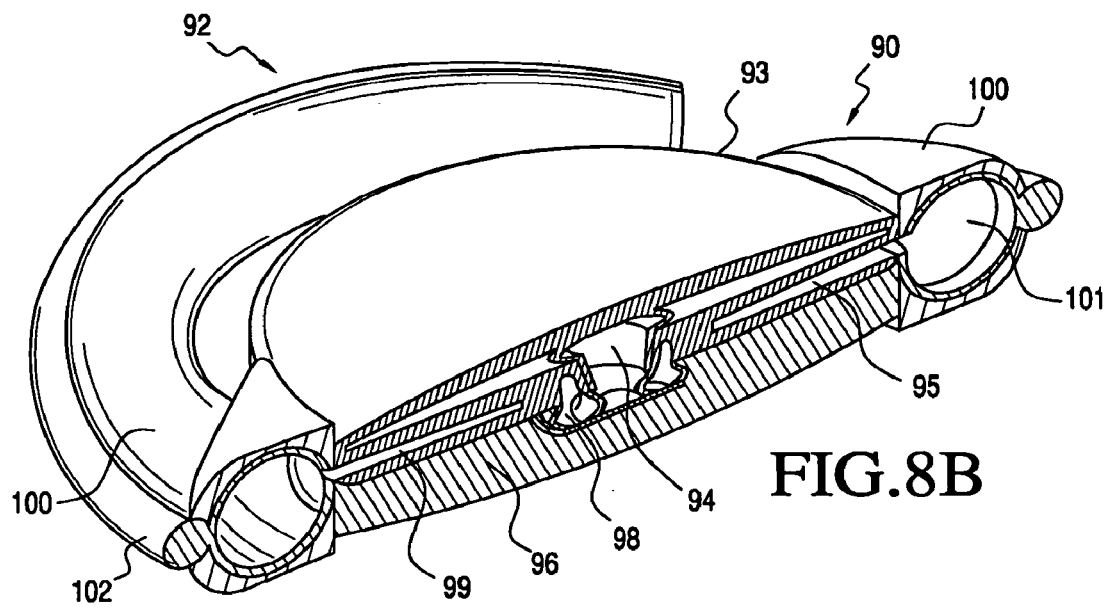

Referring now to FIGS. 8A and 8B, another alternative embodiment of an IOL constructed in accordance with the principles of the present invention is described. IOL 90 comprises optic portion 91 and haptic portion 92. Optic portion 91 comprises anterior lens element 93, primary actuator 94, intermediate layer 95 and posterior lens element 96, all formed of light-transmissive materials.

Primary actuator 94 is illustratively integrally formed with anterior lens element 93. Intermediate layer 95 includes bellows structures 97 that form secondary actuator 98. Secondary actuator 98 surrounds and is bonded to the lower portion of primary actuator 94, so that the primary and secondary actuators more in unison. Channels 99 extend from the periphery of intermediate layer to the interior of secondary actuator 98, thereby providing fluid communication between the haptic portion and the secondary actuator. As depicted in FIG. 8, the fluids in the primary and secondary actuators are not in communication.

Haptic portion 92 comprises haptics 100 and 101 that are coupled in fluid communication to optic portion 91. As depicted in FIG. 8B, each of haptics 100 and 101 has a circular cross section in the undeformed state, corresponding to maximal interior volume. Each haptic also includes a resilient support element 102, which provides the haptic with a predetermined arc in the undeformed state. Haptics 100 and 101, fluid channel 99, primary and secondary actuators 94 and 98, space 103 between anterior lens element 93 and intermediate layer 95, and space 104 between intermediate layer 95 and posterior lens element 96 all are filled with a fluid having an index of refraction selected to match the corresponding contacting structures of IOL 90.

Still referring to FIG. 8, operation of IOL 90 is now described. The undeformed state of haptics 100 and 101 corresponds to accommodated state of the lens, when the ciliary muscles are contracted and the capsule is loose. When the ciliary muscles relax, the zonules pull the capsule taut, thereby applying compressive forces to the anterior and posterior sidewalls of the haptic. These compressive forces cause the haptics to deform to a lower volume state and displacing fluid to channel 99 and the interior of secondary actuator 98. As fluid flows into the secondary actuator, it extends in the posterior direction, simultaneously reducing the fluid pressure in primary actuator 94. Reduction of fluid pressure in the primary actuator reduces the deflection of anterior lens element 93, thereby transitioning the lens to an unaccommodated condition.

As described immediately above, the primary and secondary actuators of IOL 90 provide a "reverse" accommodating action compared to the actuators of the preceding embodiments, in that the lens transitions from the accommodated to the unaccommodated states due to the displacement of fluid from the haptic portion to the optic portion of the lens. Due to the relative complexity and potential for optical aberrations arising from the presence of the primary and secondary actuators within the optic portion, it may be advantageous to relocate such mechanisms to the periphery of the optic portion of the lens. The embodiment of FIG. 9 depicts one possible implementation of such a design.

Figure 9A:
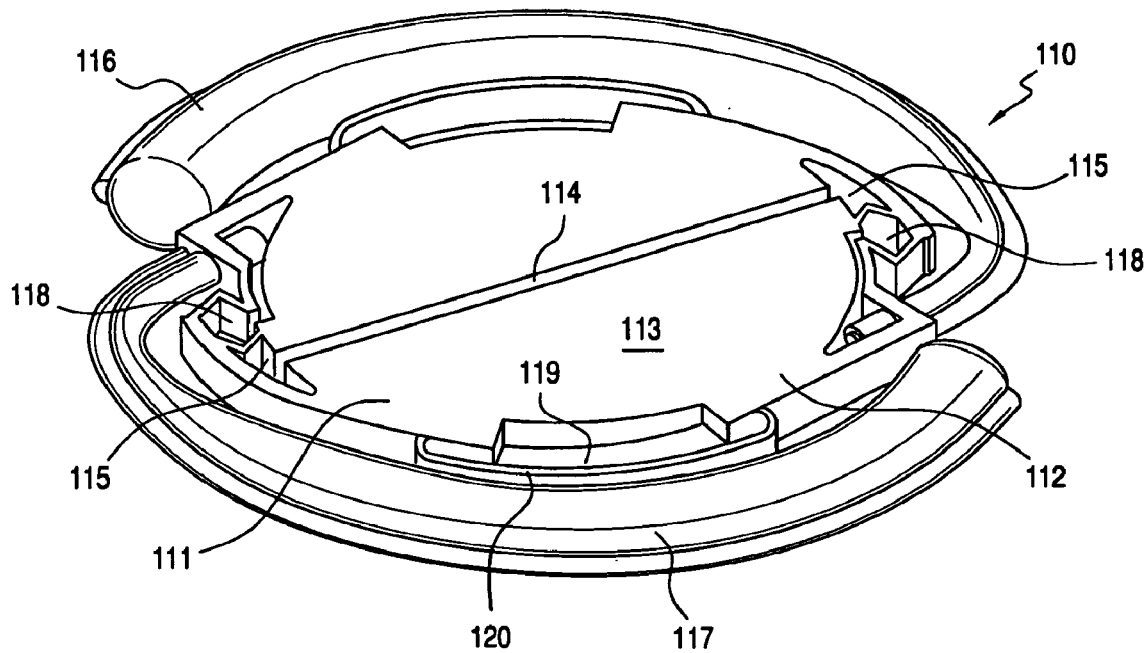
FIGS. 9A–9B are, respectively, a perspective partial view and plan view of an another alternative embodiment of the intraocular lens of the present invention.
Figure 9B:
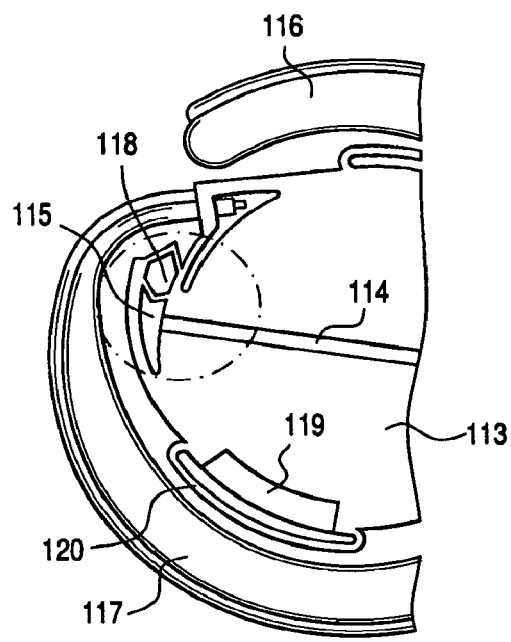

Referring now to FIGS. 9A–9B, an intraocular lens is described wherein a "reverse" accommodating action occurs responsive to displacement of fluid from the haptic portion to the optic portion of the lens. IOL 110 of FIG. 9A includes optic portion 111 and haptic portion 112. Only substrate 113 of optic portion 111 is shown, and it is to be understood the optic portion further comprises an anterior lens element, actuator and intermediate layer such as illustrated in FIG. 6A. Substrate 113 includes fluid channel 114 which is coupled at either end to reservoirs 115, which are disposed in haptic portion 112.

Haptics 116 and 117 are similar to those described for the embodiment of FIG. 8, and have a circular or other suitable cross-section that provides maximum interior volume in the undeformed state. In this manner, haptics 116 and 117 displace fluid towards the optic portion when subjected to compressive forces by the capsule during relaxation of the ciliary muscles. The end of each of haptics 116 and 117 is coupled to a bellows-like reservoir 118, which is disposed in haptic portion 112. Each reservoir 118 is separated by a wall from adjoining reservoir 115, so that pressure changes in one reservoir are communicated to the other, but there is no direct fluid communication between reservoirs 115 and 118.

In operation, compression of haptics 116 and 117 displaces fluid from the haptics flows into reservoirs 118, thereby causing the bellows-like walls of the reservoir to expand. This in turn increases the volume in the adjoining reservoir 115 and withdraws fluid from channel 114, thereby reducing the extension of the actuator and the displacement of the anterior lens element. In this manner, positive fluid flows from the haptics result in the reduction of the deflection of the anterior lens element, transitioning IOL 110 from an accommodated state to an unaccommodated state.

As also illustrated in FIGS. 9A and 9B, substrate 113 may include recesses 119 disposed at the periphery of the optic portion that communicate with expandable reservoirs 120. Recesses 119 and reservoirs 120 are configured to absorb fluid flows into and out of the space between the intermediate layer and the anterior lens element to equalize fluid pressures in that space responsive to deflection of the anterior lens element. Such reservoirs advantageously be employed in any of the preceding lens embodiments to equalize pressure differentials in interior spaces of the lenses responsive to accommodating movement of the dynamic surface of the IOL.

Figure 10A:
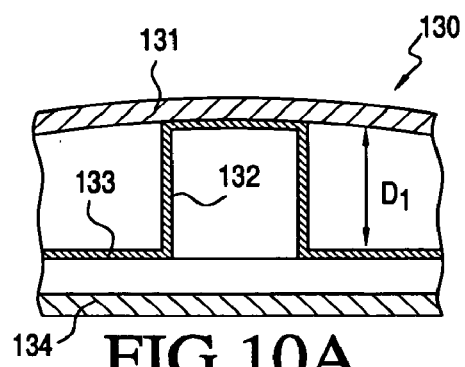
FIGS. 10A–10B are, respectively, side sectional views of an optic portion of a further embodiment of the intraocular lens of the present invention.
Figure 10B:
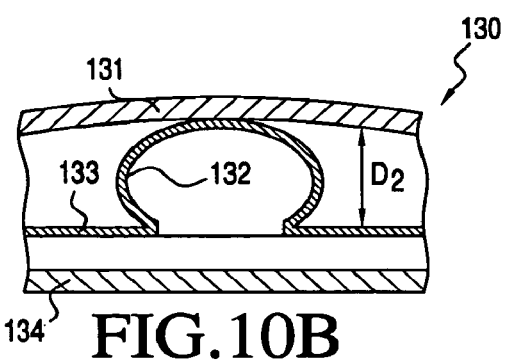

Referring now to FIGS. 10A and 10B, a further embodiment of a reverse-acting actuator of the present invention is described. FIG. 10 depict a portion of IOL 130 that includes anterior lens element 131, actuator 132, intermediate layer 133 and substrate 134. IOL 130 includes an optic portion and haptic portion as described above, wherein the haptic displaces fluid to the optic portion of the lens during relaxation of the ciliary muscles. Actuator 132 comprises an elastomeric material and may be integrally formed with, or separately formed and bonded to, intermediate layer 133. Actuator 132 is configured to deflect the anterior lens element a distance $D_1$ from the intermediate layer, corresponding to the accommodated state of IOL 130.

When the ciliary muscles relax, compressive forces applied by the capsule displace fluid from the haptic portion to the optic portion of the lens. In particular, as fluid is displaced into actuator 132, the cylindrical wall of the actuator expands to a spherical configuration, as depicted in FIG. 10B. This expansion causes actuator 132 to shorten, thereby reducing the deflection of the anterior lens element a distance $D_2$ from the intermediate layer, corresponding to the unaccommodated state of IOL 130. In this manner, IOL 130 is capable of transitioning between accommodated and unaccommodated states responsive to fluid flows between the haptic portion and optic portion of the lens.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An intraocular lens configured for implantation in a capsule following extraction of a lens, the intraocular lens being configured and adapted to accommodate in response to contraction of a patient's ciliary muscles, the intraocular lens comprising:
   a substrate having a portion defining a fluid channel;
   a lens element;
   an actuator interposed between the lens element and the substrate and in fluid communication with the fluid channel, the actuator disposed in contact with the lens element;
   a haptic having an interior volume coupled in fluid communication with the fluid channel; and
   a fluid disposed in the actuator, fluid channel and the interior volume of the haptic,
   wherein fluid is displaced between the interior volume of the haptic and the actuator to change a deflection of the lens element responsive to movement of the patient's ciliary muscles, and
   wherein a fluid-filled space is at least partially defined by an exterior surface of the actuator and the lens element.

2. The intraocular lens of claim 1 wherein the actuator is disposed along the optical axis of the intraocular lens.

3. The intraocular lens of claim 1 wherein the fluid has a refractive index substantially the same as a refractive index of the lens element, substrate and actuator.

4. The intraocular lens of claim 1 wherein, the haptic comprises a support element that provides a predetermined arc to the haptic.

5. The intraocular lens of claim 1 further comprising a ring-shaped fulcrum disposed in contact with the lens element to enhance deflection of the lens element caused by movement of the actuator.

6. The intraocular lens of claim 1 further comprising an expansion reservoir disposed at the periphery of the intraocular lens to equalize pressure differentials within the intraocular lens arising from movement of the actuator.

7. The intraocular lens of claim 1 wherein a volume of the space fluctuates during transitioning of the intraocular lens between an accommodated state and an unaccommodated state.

8. The intraocular lens of claim 1 wherein haptic has an undeformed state and a deformed state and the interior volume of the haptic is greater in the deformed state than in the undeformed state.

9. The intraocular lens of claim 8 wherein, during transitioning to the deformed state, the haptic causes fluid to be displaced from the actuator to reduce a deflection of the lens element.

10. The intraocular lens of claim 1 wherein the haptic has an undeformed state and a deformed state and the interior volume of the haptic is smaller in the deformed state than in the undeformed state.

11. The intraocular lens of claim 10 wherein, during transitioning to the deformed state, the haptic causes fluid to be displaced to the actuator to reduce a deflection of the lens element.

12. The intraocular lens of claim 11 wherein the actuator comprises a primary actuator coupled to move in unison with a secondary actuator, the secondary actuator disposed in fluid communication with the fluid channel.

13. The intraocular lens of claim 12 wherein the haptic is coupled in fluid communication to a first reservoir, the fluid channel is coupled in fluid communication to a second reservoir, and fluid displacements in the first reservoir induce corresponding fluid displacements in the second reservoir.

14. The intraocular lens of claim 13 wherein the first and second reservoirs are disposed in a haptic portion of the intraocular lens.

15. The intraocular lens of claim 11 wherein the actuator shortens when fluid is displaced from the interior volume of the haptic to the actuator.

16. The intraocular lens of claim 1 wherein a volume of the space remains constant during transitioning of the intraocular lens between an accommodated state and an unaccommodated state.

17. The intraocular lens of claim 16 wherein a peripheral zone of the lens element deflects inward during accommodation of the intraocular lens.

18. The intraocular lens of claim 1 wherein the substrate further comprises a convex anterior surface that supports the lens element with a predetermined deflection in an unaccommodated state.

19. The intraocular lens of claim 1 further comprising a barrier coating disposed within fluid channels within the intraocular lens to reduce diffusion of the fluid into the lens element or substrate.

20. The intraocular lens of claim 1 further comprising a barrier coating disposed on the exterior of the intraocular lens to reduce diffusion of body fluids into the intraocular lens.

21. An intraocular lens comprising:
   an optic portion having a lens element;
   a haptic portion coupled to the optic portion;
   an actuator disposed in contact with the lens element to selectively deflect the lens element and change an optical power of the intraocular lens;
   a haptic having an interior volume disposed in the haptic portion, displacements of fluid within the interior volume causing corresponding displacement of fluid in the actuator;
   a fluid disposed in the actuator and in the interior volume of the haptic,
   wherein forces applied to the haptic displace fluid between the interior volume and the actuator to control deflection of the lens element, and
   wherein a fluid-filled space is at least partially defined by an exterior surface of the actuator and the lens element.

22. The intraocular lens of claim 21 wherein the optic portion comprises optically transparent materials.

23. The intraocular lens of claim 21 wherein the lens element is an anterior lens element and the optic portion further comprises a posterior lens element.

24. The intraocular lens of claim 21 wherein the fluid has a refractive index substantially the same as a refractive index of the lens element and actuator.

25. The intraocular lens of claim 21 further comprising an expansion reservoir disposed at the periphery of the optic portion to equalize pressure differentials arising from movement of the actuator.

26. The intraocular lens of claim 21 wherein a volume of the space fluctuates during transitioning of the intraocular lens between an accommodated state and an unaccommodated state.

27. The intraocular lens of claim 21 wherein, further comprising a ring-shaped fulcrum disposed in contact with the lens element to enhance deflection of the lens element caused by movement of the actuator.

28. The intraocular lens of claim 21 wherein haptic has an undeformed state and a deformed state and the interior volume of the haptic is greater in the deformed state than in the undeformed state.

29. The intraocular lens of claim 28 wherein, during transitioning to the deformed state, the haptic causes fluid to be displaced from the actuator to reduce a deflection of the lens element.

30. The intraocular lens of claim 21 wherein haptic has an undeformed state and a deformed state and the interior volume of the haptic is smaller in the deformed state than in the undeformed state.

31. The intraocular lens of claim 30 wherein, during transitioning to the deformed state, the haptic causes fluid to be displaced to the actuator to reduce a deflection of the lens element.

32. The intraocular lens of claim 31 wherein the actuator comprises a primary actuator coupled to move in unison with a secondary actuator, the secondary actuator disposed in fluid communication with the fluid channel.

33. The intraocular lens of claim 31 wherein the haptic is coupled in fluid communication to a first reservoir, the fluid channel is coupled in fluid communication to a second reservoir, and fluid displacements in the first reservoir induce corresponding displacements in the second reservoir.

34. The intraocular lens of claim 33 wherein the first and second reservoirs are disposed in a haptic portion of the intraocular lens.

35. The intraocular lens of claim 31, wherein the actuator shortens when fluid is displaced from the interior volume of the haptic to the actuator.

36. The intraocular lens of claim 21 wherein a volume of the space remains constant during transitioning of the intraocular lens between an accommodated state and an unaccommodated state.

37. The intraocular lens of claim 21 wherein a peripheral zone of the lens element deflects inward during accommodation of the intraocular lens.

38. The intraocular lens of claim 21 wherein the optic portion comprises a convex surface that supports the lens element with a predetermined deflection in an unaccommodated state.

39. The intraocular lens of claim 21 further comprising a barrier coating disposed within fluid channels within the intraocular lens to reduce diffusion of the fluid into the lens element or substrate.

40. The intraocular lens of claim 21 further comprising a barrier coating disposed on the exterior of the intraocular lens to reduce diffusion of body fluids into the intraocular lens.

* * * * *